(12) United States Patent
Seifert (10) Patent No.: US 8,647,262 B2
(45) Date of Patent: Feb. 11, 2014

(54) DEFLECTABLE TIP VIDEOARTHROSCOPE

(75) Inventor: Alexander Seifert, Naples, FL (US)

(73) Assignee: Arthrex, Inc., Naples, FL (US)

( * ) Notice: Subject to any disclaimer, the term of this patent is extended or adjusted under 35 U.S.C. 154(b) by 1554 days.

(21) Appl. No.: 11/783,090

(22) Filed: Apr. 5, 2007

(65) Prior Publication Data

US 2007/0249899 A1    Oct. 25, 2007

(51) Int. Cl.
  *A61B 1/00*   (2006.01)
  *A61B 1/06*   (2006.01)
  *A61B 1/04*   (2006.01)

(52) U.S. Cl.
  USPC ............ 600/146; 600/173; 600/137; 600/109

(58) Field of Classification Search
  USPC .......... 600/109, 114, 131, 144, 171, 137, 146
  See application file for complete search history.

(56) References Cited

U.S. PATENT DOCUMENTS

| | | | | |
|---|---|---|---|---|
| 3,256,875 A * | 6/1966 | Tsepelev et al. | ............... | 600/148 |
| 4,327,735 A | 5/1982 | Hampson | | |
| 4,779,612 A * | 10/1988 | Kishi | ............................ | 600/141 |
| 5,337,734 A * | 8/1994 | Saab | .............................. | 600/121 |
| 5,379,756 A * | 1/1995 | Pileski et al. | ................. | 600/109 |
| 5,481,406 A * | 1/1996 | Yamazaki et al. | ............. | 359/694 |
| 5,538,497 A * | 7/1996 | Hori | .............................. | 600/182 |
| 5,621,830 A * | 4/1997 | Lucey et al. | ..................... | 385/25 |
| 5,651,759 A * | 7/1997 | Leiner et al. | ................... | 600/182 |
| 5,807,237 A * | 9/1998 | Tindel | ........................... | 600/114 |
| 5,978,161 A | 11/1999 | Lemke | | |
| 6,364,830 B1 | 4/2002 | Durell | | |
| 6,447,445 B1 | 9/2002 | Hirano | | |
| 6,500,115 B2 * | 12/2002 | Krattiger et al. | ............... | 600/173 |
| 7,815,564 B2 * | 10/2010 | Geitz et al. | ..................... | 600/107 |
| 8,409,175 B2 * | 4/2013 | Lee et al. | ........................... | 606/1 |
| 2002/0099263 A1 * | 7/2002 | Hale et al. | ...................... | 600/117 |
| 2002/0128538 A1 * | 9/2002 | Thompson | ..................... | 600/121 |
| 2002/0184122 A1 | 12/2002 | Yamaguchi et al. | | |
| 2003/0004397 A1 | 1/2003 | Kameya et al. | | |
| 2003/0040657 A1 * | 2/2003 | Yamaya et al. | ............... | 600/107 |
| 2004/0073084 A1 | 4/2004 | Maeda et al. | | |
| 2005/0154262 A1 | 7/2005 | Banik et al. | | |
| 2006/0022234 A1 | 2/2006 | Adair et al. | | |
| 2007/0284373 A1 * | 12/2007 | Okuchi | ......................... | 220/262 |
| 2008/0045794 A1 * | 2/2008 | Belson | .......................... | 600/145 |
| 2008/0167524 A1 * | 7/2008 | Goldwasser et al. | ......... | 600/115 |

FOREIGN PATENT DOCUMENTS

| | | |
|---|---|---|
| DE | 197 50 698 A1 | 5/1998 |
| EP | 0 498 114 A1 | 8/1992 |

* cited by examiner

*Primary Examiner* — Philip R Smith
*Assistant Examiner* — William Chou
(74) *Attorney, Agent, or Firm* — Dickstein Shapiro LLP (57) ABSTRACT

A deflectable tip videoarthroscope of 5.4 mm diameter or smaller, comprising a miniaturized chip-in-tip CCD with four-way angulations mounted on the distal end of the arthroscope. The deflectable tip videoarthroscope may be provided with a replaceable distal window made of a thin material (such as polycarbonate or acrylic) or a glass (sapphire or other) with very high light transmission properties, connected to a sheathing system that is disposable or limited-reusable, which could be discarded if a shaver burr or ablation probe contacts the lens. This design protects the distal window of the videoarthroscope during use and reduces scope repair costs and system down-time. The deflectable tip videoarthroscope may additionally include a steering wheel, which allows 360 degree rotation of the instrument during arthroscopic procedures. The videoarthroscope may further include an irrigation channel or a wireless imager control system.

12 Claims, 6 Drawing Sheets

DEFLECTABLE TIP VIDEOARTHROSCOPE

CROSS REFERENCE TO RELATED APPLICATIONS

This application claims the benefit of U.S. Provisional Application No. 60/789,167, filed Apr. 5, 2006.

FIELD OF THE INVENTION

The present invention relates to instruments for arthroscopic surgery and, more particularly, to videoarthroscopes.

BACKGROUND OF THE INVENTION

Orthopedic physicians are frequently challenged when performing arthroscopic surgery because of the limitations of the design and technology of the optical/video systems and instruments. The goal of arthroscopy is to perform minimally invasive surgery as an alternative to open surgery. Arthroscopy has proven to be safer, less painful and have a faster recovery time for patients when compared to open surgery. However, to duplicate the effectiveness of open surgery, which offers a three-dimensional perspective of the joint, a physician must adapt to a more challenging technique, using rigid scopes and a camera that transmits a video image onto a two-dimensional television or LCD monitor. Thus, the currently available conventional arthroscopic equipment poses some major challenges for physicians.

For example, conventional rod-lens arthroscopes are linear in design and a physician must steer this direct vector tool inside the joint in order to use the scope. These arthroscopes have an objective lens that is tilted in a fixed plane, e.g., 30, 45, or 70 degrees off the center line of the scope. This scope design forces the physician to use triangulation techniques with the scopes and instruments in order to operate on a target area in the joint. Considering the space constraints, the patient's anatomy, and the complexity of repair that may need to be performed, rigid arthroscopes do not easily allow 360 degrees of visualization inside the joint without switching to different portals or scope angles. This often makes it difficult for a physician to orient himself correctly, perform a proper diagnosis of anatomy and pathology, or visualize his instruments as they are being introduced into or used within the joint.

In addition, since conventional arthroscopes are linear in design, they are typically rigid and do not allow for any flexibility of movement around anatomical structures. However, human joint cavities are not composed of straight vectors and right-angled corners. Instead, the natural geometry inside human joints is a web of curved bones, condyles, and uneven articular surfaces held together by ligaments and tendons at various anatomical attachment points. Hence, rigid scopes and instruments limit the mobility and access of physicians into all areas of the joint, which affects a physician's ability to perform the best, or at least the most efficient, repair possible.

Other limitations of current optics/scopes and instruments include the fact that linear/direct-vector scopes and instruments are not able to reach all areas of the joint, especially when steering over or around anatomic structures. Rod-lens arthroscopes are also fragile and are easily damaged by reprocessing, handling and intra-operative use. They are also prone to fogging, scratched lenses and material build-up on the windows, all of which reduce image quality.

Another limitation of conventional scopes relates to the optical chain, which is composed of three separate components: the scope, the light cable, and the camera head. This design is cumbersome and inefficient for today's standards because all three components must be purchased separately, sterilized, and then assembled for surgery. If a scope with a different angle of view is needed, the surgery must be interrupted as one scope is detached from the light cord and camera head and is replaced with a greater/higher angled scope, as needed.

Further, conventional video/optical chains use redundant cables, one for the fiber optic light cable (for light transmission) and another for the camera cable. Excessive cables in the sterile field clutter workflow and operating room efficiency, as well as increase the risk of cable damage during daily use, cleaning/handling and sterilization.

Video resolution may be lost using a conventional rod-lens scope and camera head because the joint cavity must first be illuminated through a series of fiber optic bundles (light cable and the scope). Then the image is transmitted through the scope windows, rod lenses, and bulky couplers into the camera head (either 1-chip or 3-chip) before the image is finally sent electronically to the camera processor. If any one of the components in this optical chain is dirty, not working correctly, or slightly damaged, the resolution and image quality sent to the monitor or peripheral devices is compromised. Additionally, most rod-lens arthroscopes only allow approximately 250-300 horizontal lines of resolution to the camera head.

The scopes, light cables, and camera heads offered by most surgical companies are not durable enough for autoclave sterilization. Most medical facilities enjoy the time efficiency, cost savings, and safety of steam autoclaving. Companies that do not offer an autoclave compatible video/optical chain are not meeting the needs of the global orthopedic customer market. This is especially true in the largest arthroscopy markets such as the United States' ambulatory surgery center market, and the healthcare systems in Europe, Japan, and Australia, where government health regulations have eliminated liquid soaking methods as an acceptable form of equipment sterilization.

Accordingly, there exists a need for a videoarthroscope that overcomes the problems and limitations of the conventional arthroscopes previously discussed.

SUMMARY OF THE INVENTION

The present invention provides a 30 degree angled deflectable tip videoarthroscope of 5.4 mm diameter or smaller comprising a miniaturized chip-in-tip CCD with four-way angulations mounted on the distal end of the arthroscope. The deflectable tip videoarthroscope of the present invention may be provided with a replaceable distal window made of a thin material (such as polycarbonate or acrylic) or a glass (sapphire or other) with very high light transmission properties, connected to a sheathing system that is disposable or limited-reusable. This replaceable window/sheath could be discarded if a shaver burr or ablation probe contacts the lens. This design would protect the distal window of the videoarthroscope during use and would reduce scope repair costs and system down-time. Optionally, the deflectable tip videoarthroscope of the present invention additionally comprises a steering wheel, which allows 360 degree rotation of the instrument during arthroscopic procedures.

The present invention also provides a method of capturing images with a deflectable tip videoarthroscope used during an arthroscopic procedure. The method of the present invention comprises the steps of (i) providing a videoarthroscope in the proximity of a surgical site undergoing an arthroscopic procedure, the videoarthroscope having a deflectable tip using a 30 degree angled, distally mounted, miniaturized chip-in-tip CCD with four-way angulations, the videoarthroscope optionally comprising at least one structural element selected from the group consisting of a removable distal window, a two-position retractable scope sheath that allows the sheath to be used either in a Rigid Mode or in a Flex Mode, a steering wheel that allows 360 degree rotation of the instrument during arthroscopic procedures, and an additional miniaturized CCD located on or within the videoarthroscope handle; and (ii) capturing at least one image of the arthroscopic surgical site with the deflectable tip videoarthroscope.

The present invention also provides a method of conducting an arthroscopic surgical procedure using a deflectable tip videoarthroscope. The method comprises the steps of (i) providing a videoarthroscope comprising a deflectable tip using a 30 degree angled, distally mounted, miniaturized chip-in-tip CCD with four-way angulations, the videoarthroscope optionally comprising at least one structural element selected from the group consisting of a removable distal window, a two-position retractable scope sheath that allows the sheath to be used either in a Rigid Mode or in a Flex Mode, a steering wheel that allows 360 degree rotation of the instrument during arthroscopic procedures, and an additional miniaturized CCD mounted on or within the videoarthroscope handle; (ii) positioning the videoarthroscope in the proximity of a surgical site undergoing an arthroscopic procedure; and (iii) employing the deflectable tip videoarthroscope to conduct the arthroscopic procedure.

Other features and advantages of the present invention will become apparent from the following description of the invention which refers to the accompany drawings.

DESCRIPTION OF THE INVENTION

The present invention provides a 30 degree angled deflectable tip videoarthroscope using a miniaturized CCD with four-way angulations mounted on the tip of the instrument. Preferably, the deflectable tip videoarthroscope of the present invention may be provided with a distal window made of a thin material (such as polycarbonate or acrylic) or a glass (sapphire or other) with very high light transmission properties, connected to a sheathing system that is disposable or limited-reusable. This replaceable window/sheath could be discarded if a shaver burr or ablation probe contacts the lens. This design would protect the distal window of the videoarthroscope during use and would reduce scope repair costs and system down-time. Preferably, the deflectable tip videoarthroscope may further comprise a steering wheel, which allows 360 degree rotation of the instrument during arthroscopic procedures with an integrated electronic of manual CCD horizontal image stabilization system.

The invention also provides a method of capturing images with a deflectable tip videoarthroscope used during an arthroscopic procedure. The method of the present invention comprises the steps of (i) providing a videoarthroscope in the proximity of an arthroscopic surgical site, the videoarthroscope having a deflectable tip using a 30 degree angled distally mounted miniaturized chip-in-tip CCD with four-way angulations, the videoarthroscope optionally comprising at least one structural element selected from the group consisting of a removable distal window, a two-position retractable scope sheath that allows the sheath to be used in a Rigid Mode and then retracted for use in a Flex Mode, a steering wheel that allows 360 degree rotation of the instrument during arthroscopic procedures, and an additional miniaturized CCD mounted on or within the videoarthroscope handle; (ii) capturing at least one image of the arthroscopic surgical site with the deflectable tip videoarthroscope; and conducting the arthroscopic procedure.

The all-in-one flexible/deflectable tip videoarthroscope camera of the present invention (described in more detail below) uses a 30 degree angled distally mounted miniaturized chip-in-tip CCD (either digital CCD, high-definition CCD or CMOS imager) with four-way angulation, allowing a physician to have improved access to pathology in the joint when compared with direct-vector (straight/rigid) rod-lens arthroscopes and linear instrumentation.

The deflectable tip videoarthroscope of the invention provides a multi-axis visualization inside the joint, thus permitting real-time 360 degrees of visualization and access around the joint and target repair area, and generating a holistic view of the anatomy, pathology, and repairs required. The highly efficient all-in-one integrated videoarthroscope camera is more efficient to assemble, use, troubleshoot, repair and sterilize compared to the conventional assembly of three to five distinct components. There is less videoarthroscope redundancy to facilitate. Further, the deflectable tip videoarthroscope 100 of the present invention offers cost containment through one videoarthroscope system that serves the purpose of three to five separate components and scopes used in each arthroscopic procedure.

Figure 1:
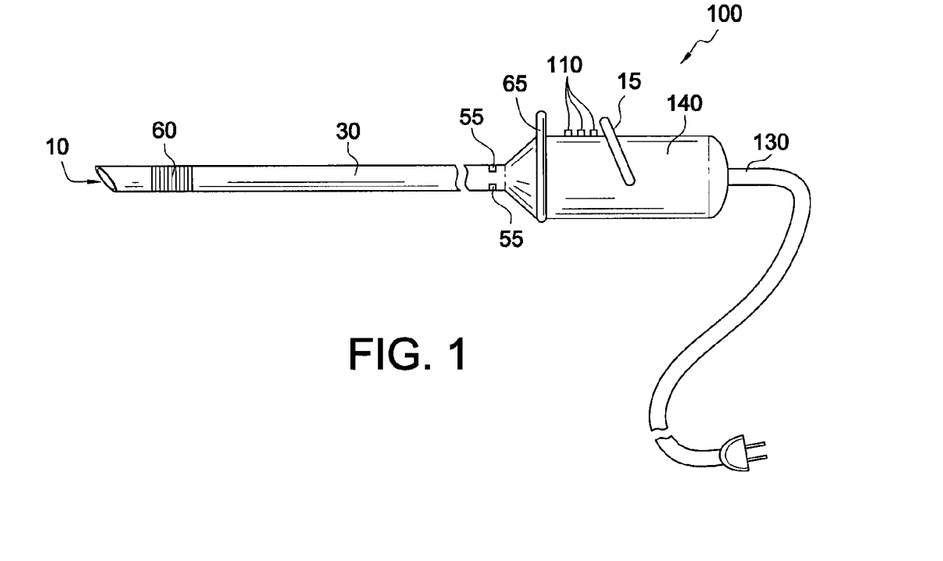
FIG. 1 illustrates an exemplary embodiment of a videoarthroscope of the present invention.

Referring now to the drawings, where like elements are designated by like reference numerals, FIG. 1 illustrates an exemplary embodiment of a deflectable tip videoarthroscope 100 of the present invention. The deflectable tip videoarthroscope 100 comprises a camera head 140 with camera buttons 110 and camera cable 130, scope shaft 30 including deflectable tip 60 with a 30 degree angled objective lens 10, and sheath connection posts 55. The objective lens 10 allows use of the videoarthroscope as a conventional scope in "Rigid Mode" or as a flexible tip scope in "Flex Mode." The invention allows deflection of the objective lens 10 through a full spectrum of viewing angles (from about 30 to about 120 degrees of flexion) on demand by way of deflection handle 15, without interrupting surgery, exchanging scopes or risking disorientation of the physician. The videoarthroscope 100 also includes a steering post 65 for controlling the flexible tip 60.

Figure 2:
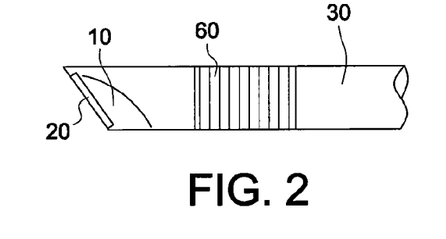
FIG. 2 illustrates a close-up partial view of a distal window of the videoarthroscope of FIG. 1.

FIG. 2 illustrates a close-up view of the distal end of another exemplary embodiment of a deflectable tip videoarthroscope 100 of the invention including an interchangeable/removable distal window 20, preferably a sapphire distal window. The interchangeable distal window 20 reduces repair costs, customer frustration, and surgery down-time if the objective lens 10 is scratched or damaged because the distal window 20 of the videoarthroscope 100 can be quickly replaced.

Figure 3A:
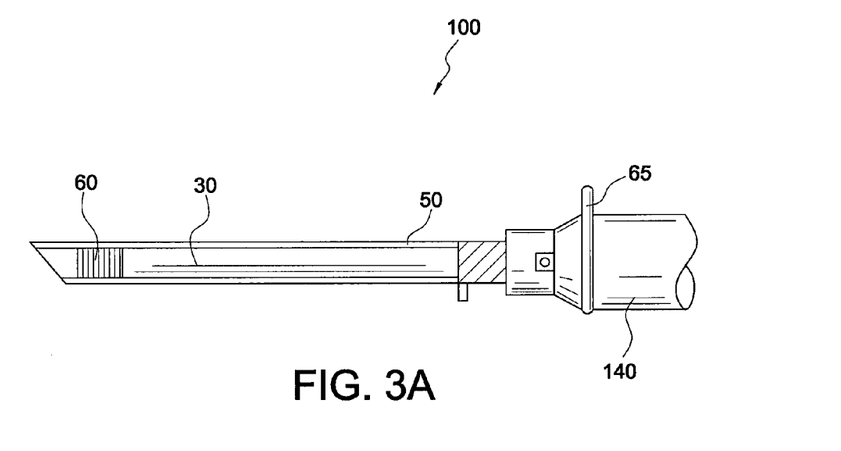
FIGS. 3A and 3B illustrate exemplary embodiments of a videoarthroscope of the present invention with a rigid and a flexible sheath, respectively.
Figure 3B:
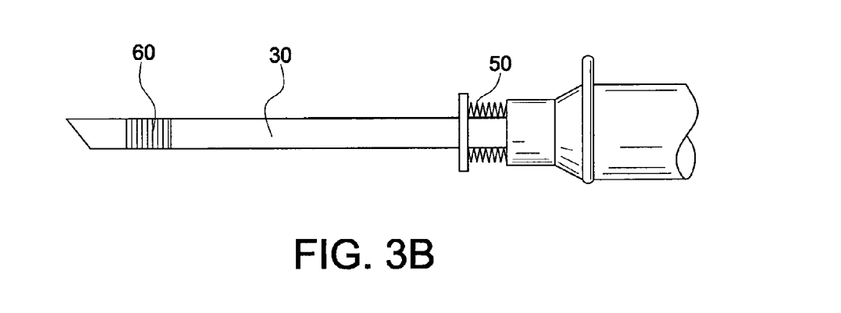
Figure 8:
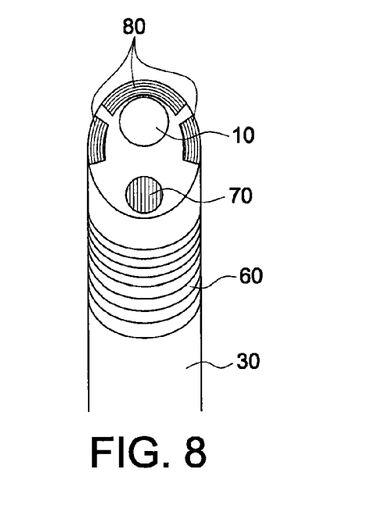
FIG. 8 illustrates a close-up partial view of the distal end of the videoarthroscope of FIG. 7.

FIGS. 3A and 3B illustrate another exemplary embodiment of a deflectable tip videoarthroscope 100 of the present invention comprising a two-position retractable sheath 50 having a Rigid Mode (FIG. 3A) and a Flex Mode (FIG. 3B). FIG. 3A also illustrates the sheath 50 being used to protect the scope 100. In Rigid Mode, the physician may use the system like a conventional rigid arthroscope. As shown in FIG. 3B, the sheath 50 retracts and exposes the scope 100 while in "Flex Mode." Whether in Flex Mode or Rigid Mode, the sheath 50 also provides fluid into the joint space and/or allows delivery of flexible instrumentation or RF probes through optional irrigation/instrument channel 70 (FIG. 8). The scope 100 may also include fiber optic light bundles 80 to provide light for the camera.

Figure 4A:
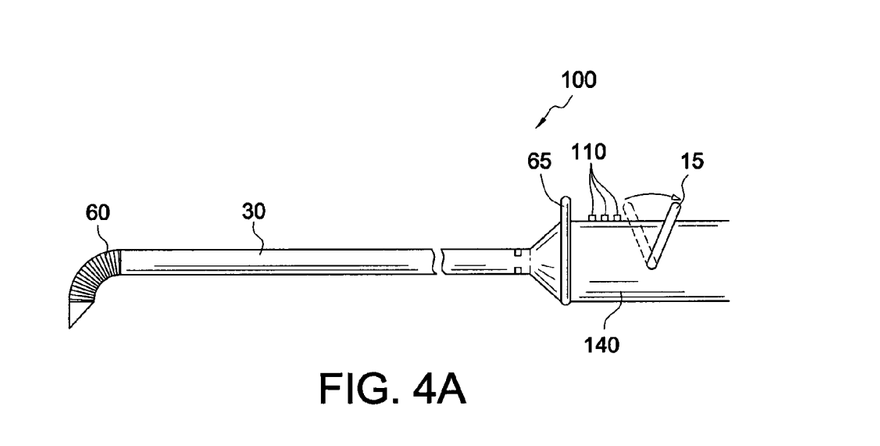
FIGS. 4A and 4B illustrate exemplary embodiments of a deflectable tip videoarthroscope of the present invention with a deflectable tip at different angulations.
Figure 4B:
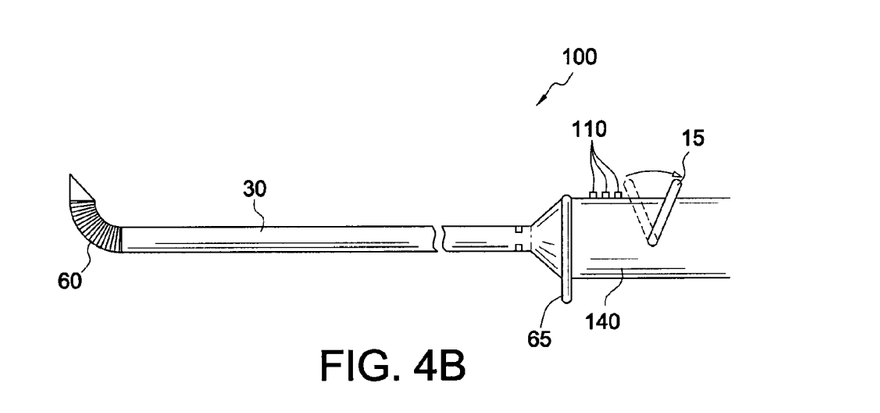

FIGS. 4A and 4B illustrate the four-way angulations of a deflectable tip 60 of the videoarthroscope 100 of the present invention. Using a steering post 65, the tip 60 of the videoarthroscope 100 is steered in the up, down, left, or right direction, with the objective lens 10 being directed accordingly by the deflection handle 15.

Figure 5:
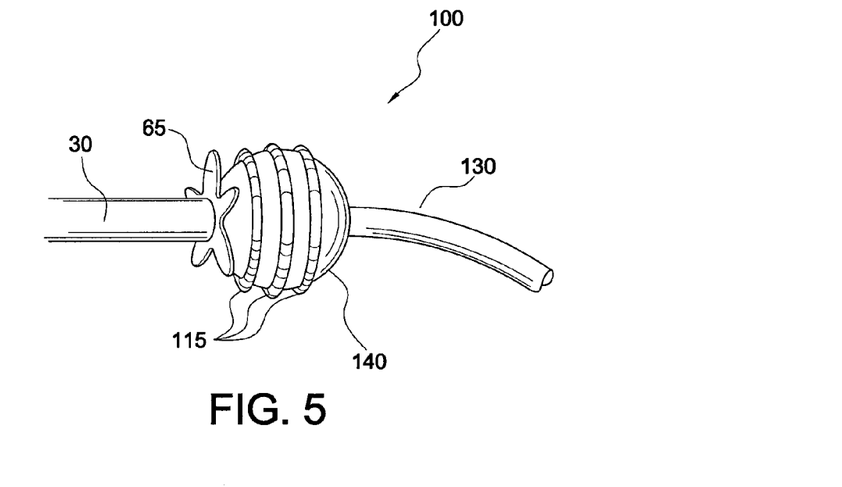
FIG. 5 illustrates a close-up partial view of camera control buttons of an exemplary embodiment of the present invention.

FIG. 5 illustrates a close-up of the camera head 140 portion of a videoarthroscope 100 of another embodiment of the invention. This embodiment provides an alternative to the camera head buttons 110 of FIG. 1. Instead, the camera may be controlled using a series of three raised rings 115 (almost like donut rings) that physicians could independently squeeze to trigger remote digital image capture, video or perform other programmable camera functions. The benefit of having a series of pronounced/raised rings 115 around the entire camera handle 140 construct eliminates the need to search for the button heads 110 during surgery in a dark operating room which is a common problem with all camera systems.

Figure 6:
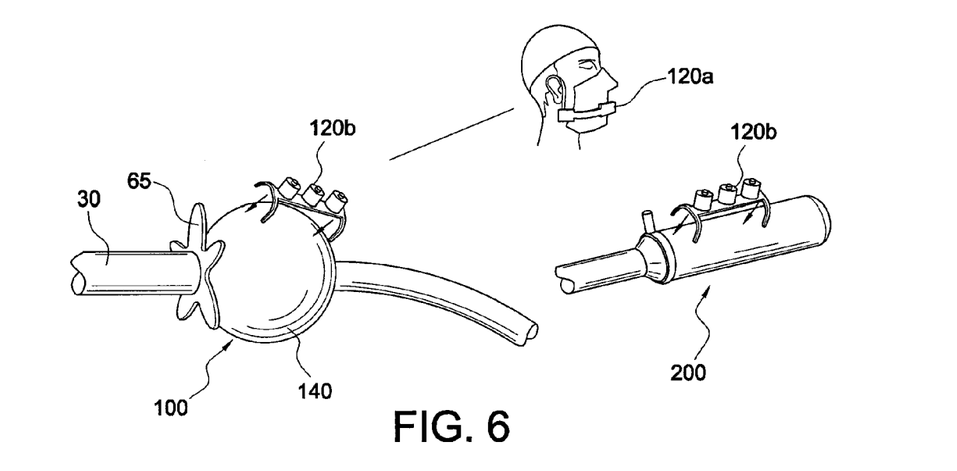
FIG. 6 illustrates a close-up partial view of a wireless camera control system of an exemplary embodiment of the present invention.

FIG. 6 illustrates a close-up of the camera head 140 portion of a videoarthroscope 100 of yet another embodiment of the invention. As an additional alternative to camera head buttons 110 would be removing the buttons 110 completely from the camera head 140 and incorporating a wireless triggering system 120—such as voice activation through a wireless headset microphone 120a, a clip on wireless device (using magnets or a clip system) with buttons 120b (either disposable or reusable) that could be attached to the camera cable 130, camera head 140, shaver 200 or any other device, using evolving wireless technology (such as Blue-tooth, Infra-red, etc.). The benefit here is that the physician could assume hands free control of the triggering function or they could pass it on to their assistant, nurse, technician, etc.

Figure 7:
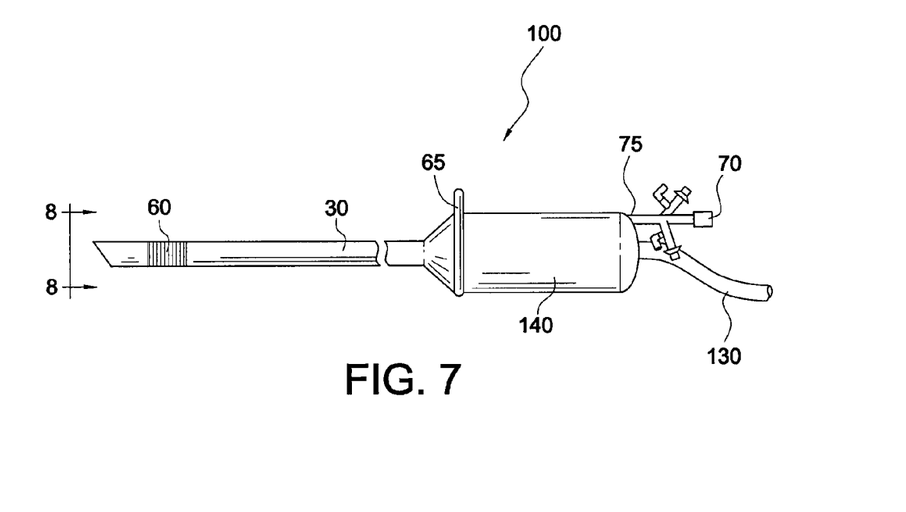
FIG. 7 illustrates an exemplary embodiment of a videoarthroscope of the present invention.

FIGS. 7 and 8 illustrate yet another embodiment of the present invention. In the embodiment of FIGS. 7 and 8, a streamlined irrigation channel 70 runs through the centerline of the videoarthroscope 100 to provide irrigation into the joint and help clear the optical surface of the lens 10. Irrigation would be connected at the back of the videoarthroscope handle through a removable 3-pronged stop-cock system 75. The channel 70 could also be used to deliver flexible devices (electrocautery probes or other flexible devices) or other fluids.

Figure 9:
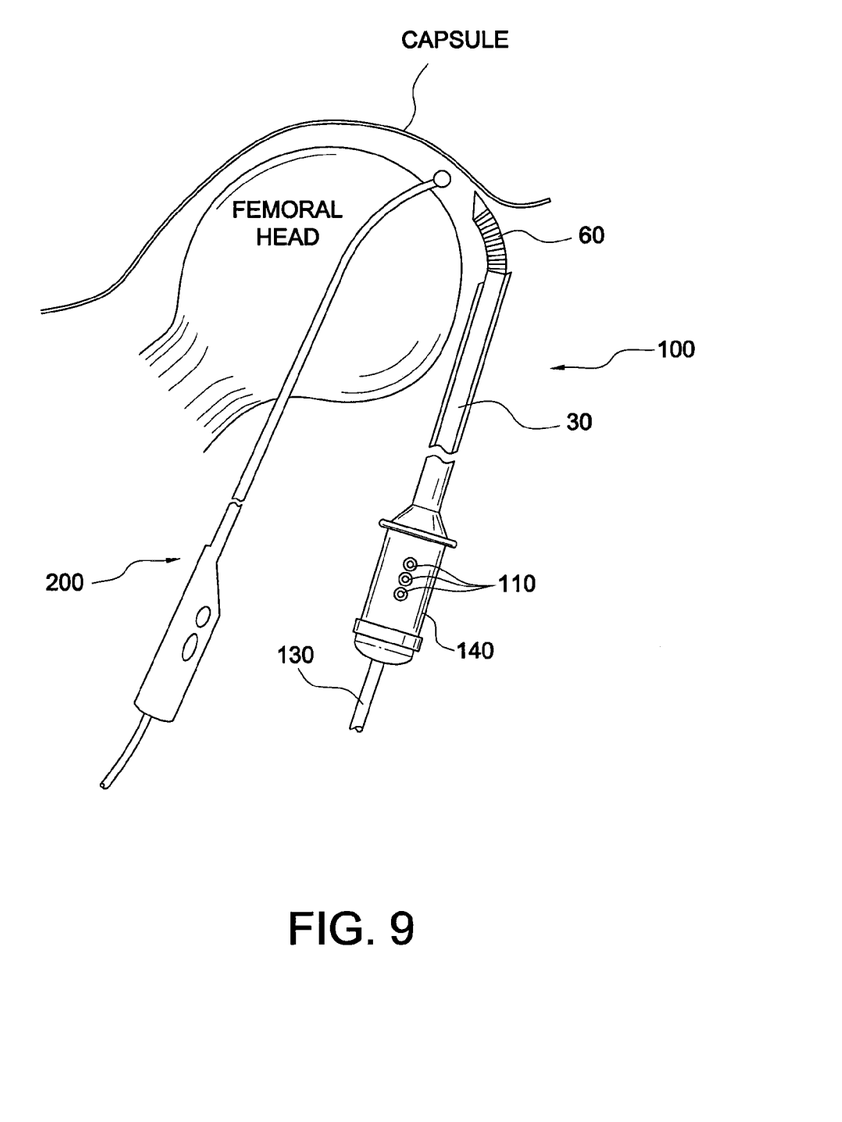
FIG. 9 illustrates the use of a videoarthroscope of the present invention during an arthroscopic procedure.

FIG. 9 illustrates the videoarthroscope 100 of the present invention during an arthroscopic surgery, for example, during access to a joint cavity or capsule. The combined use of the videoarthroscope 100 with steerable flexible RF probes, shaver blades instruments, etc. 200, offer physicians the options to repair and resect soft tissue or bone, where it was previously not possible or difficult to perform with rigid scopes and instruments.

In all the above-described embodiments, optimized high-definition digital video resolution transmission through miniaturized CCD technology offers the same true color rendition, clarity and brightness of a three-chip camera, but is packaged in a single-chip sized CCD. The videoarthroscope 100 of the present invention creates a comprehensive portfolio of maneuverable products that offer greater variety and flexibility of techniques for arthroscopic soft tissue and bone repair.

In one exemplary embodiment, the design specifications of the videoarthroscope 100 of the invention are as follows. There is a removable window cap 20 (with or without working channel sheath) and an outer diameter of 4 mm. The videoarthroscope 100 includes a working length of 180 mm, directions of view in Rigid Mode of 25-30 degrees off the center line, and a deflection of tip 60 in Flex Mode of a minimum of 90 degrees with a four-way angulation. In addition, the videoarthroscope 100 of the present invention includes a field of view of a minimum of 90 degrees, although, in a preferred embodiment, the field of view is about 115 degrees. The videoarthroscope 100 also comprises a steering mechanism having an image rotation/steering wheel 65 built into the handle to allow 360 degree rotation of the instrument along the longitudinal axis. The videoarthroscope 100 may also include a light cable of fiber optic light transmission bundles 80 incorporated into the handle 140 and camera cable 130, which is bifurcated at the camera/light source junction. Additionally, the videoarthroscope 100 comprises an image sensor (not shown), such as a CCD imager, and three or four camera buttons 110, 115, 120b that are programmable through a camera processor.

In another exemplary embodiment, the design specifications of the videoarthroscope 100 further include the movable sheath 50 thereby allowing for two modes of operation, a continuous flow or a conventional arthroscope. The working length would be 180 mm in Rigid Mode, which detracts to about 160 mm in Flex Mode with single or dual rotating stopcocks. The retractable cannula would include trocar spikes with either a triangular tip (sharp) or a blunt tip (blunt pencil design) in order to introduce the cannula into the joint space.

The videoarthroscope 100 of the present invention may be employed during various arthroscopic procedures to provide improved visualization in such procedures. For example, in hip arthroscopy, there can be access over, around the femoral head, and into deep recesses of hip capsule (an area where loose bodies accumulate and/or where many soft tissue lesions occur). In shoulder arthroscopy, the system of the present invention allows complete diagnostic through a single portal, avoiding the complication of switching between multiple portals in order to visualize different areas of the joint. The videoarthroscope 100 of the present invention is the first visualization tool that allows a multi-planar view over the repair site for tissue anchors and suture passing techniques and any area inside the joint. In ankle arthroscopy, the videoarthroscope 100 of the present invention allows navigating over the talar dome and into the lateral gutter. In knee arthroscopy, such as PCL and ACL reconstructions, the videoarthroscope 100 allows access to all deep recesses of the joint cavity that are difficult to reach with rigid scopes.

The videoarthroscope 100 of the present invention may be manufactured using current technology to withstand steam autoclaving, various liquid soaking methods and gas plasma sterilization. As noted above, a CCD chip or CMOS chip imaging sensor could be mounted at the tip of the videoarthroscope in conjunction with manual or electronic horizontal image stabilization technology (which maintains the CCD or CMOS chip in a position horizontal to the ground), allowing the physician to maneuver the deflectable tip camera inside the joint and not lose orientation.

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting. Additions, deletions, substitutions, and other modifications can be made without departing from the spirit or scope of the present invention.

What is claimed as new and desired to be protected by Letters Patent of the United States is:

1. A videoarthroscope comprising:
    a camera head with camera control buttons arranged as continuous rings around the camera head, wherein the camera control buttons control operation of an imager;
    a scope shaft, extending from the camera head;
    a deflectable tip at the end of the scope shaft, the deflectable tip terminating in a 30 degree angled objective lens and a single flexible portion located between the deflectable tip and the scope shaft;
    the imager being mounted at a distal end of the deflectable tip; and
    a removable window arranged at the distal end of the angled objective lens of the deflectable tip, such that the imager can take images through the window, wherein
    the deflectable tip is allowed a complete 360 degree rotation along a longitudinal axis by use of a steering mechanism comprising a single deflection handle and a single steering post, wherein the steering mechanism bends the single flexible portion of the deflectable tip, and wherein the single deflection handle deflects the deflectable tip a minimum of 90 degrees and wherein the single steering post is capable of a complete 360 degree rotation to allow the deflectable tip of the videoarthroscope to be steered in the up, down, left or right direction or in any other direction of its complete 360 degree rotation.

2. The videoarthroscope of claim 1, further comprising a camera cable attached to the camera head.

3. The videoarthroscope of claim 1 further comprising a retractable sheath configured to extend over the scope shaft, thereby allowing the videoarthroscope to be used in a flexible mode or a rigid mode.

4. The videoarthroscope of claim 1 further comprising a steering wheel.

5. The videoarthroscope of claim 1 wherein the imager is a miniaturized CCD imager.

6. The videoarthroscope of claim 1 wherein the imager is a CCD or CMOS chip.

7. The videoarthroscope of claim 1 wherein the removable window comprises one of polycarbonate, acrylic, sapphire, or other glass.

8. The videoarthroscope of claim 1, wherein the imager is controlled by a wireless control system.

9. The videoarthroscope of claim 8, wherein the wireless control system comprises a wireless headset microphone.

10. The videoarthroscope of claim 8, wherein the wireless control system comprises a clip on wireless device with buttons.

11. The videoarthroscope of claim 1, further comprising fiber optic light transmission bundles.

12. The videoarthroscope of claim 1, further comprising an irrigation channel running though the scope shaft.

* * * * *